(12) United States Patent
Wakita

(10) Patent No.: US 7,423,246 B2
(45) Date of Patent: Sep. 9, 2008

(54) ANALYSIS APPARATUS AND ANALYSIS DISC USED FOR THE SAME

(75) Inventor: Tsugio Wakita, Matsuyama (JP)

(73) Assignee: Matsushita Electric Industrie Co., Ltd., Osaka (JP)

( * ) Notice: Subject to any disclaimer, the term of this patent is extended or adjusted under 35 U.S.C. 154(b) by 779 days.

(21) Appl. No.: 10/518,028

(22) PCT Filed: May 29, 2003

(86) PCT No.: PCT/JP03/06790

§ 371 (c)(1), (2), (4) Date: Dec. 15, 2004

(87) PCT Pub. No.: WO04/001396

PCT Pub. Date: Dec. 31, 2003

(65) Prior Publication Data

US 2005/0259260 A1    Nov. 24, 2005

(30) Foreign Application Priority Data

Jun. 19, 2002    (JP) .............................. 2002-177828

(51) Int. Cl.
G02B 7/04 (2006.01)
G11B 7/00 (2006.01)

(52) U.S. Cl. .................................. 250/201.5; 369/116

(58) Field of Classification Search .............. 250/201.5, 250/205; 369/53.2, 53.31, 106, 116, 124.07, 369/134

See application file for complete search history.

(56) References Cited

U.S. PATENT DOCUMENTS

2003/0224457 A1 * 12/2003 Hurt et al. ..................... 435/7.2

FOREIGN PATENT DOCUMENTS

| JP | 2-269938 | 11/1990 |
|---|---|---|
| JP | 3-225278 | 10/1991 |
| JP | 4-233462 | 8/1992 |
| JP | 5-5741 | 1/1993 |
| JP | 7-209185 | 8/1995 |
| JP | 10-320855 | 12/1998 |
| WO | WO 96/09548 | 3/1996 |
| WO | WO99/24822 | 5/1999 |

* cited by examiner

Primary Examiner—Thanh X Luu
(74) Attorney, Agent, or Firm—Steptoe & Johnson LLP (57) ABSTRACT

It is an object of the present invention to provide an analysis apparatus which can achieve an image with a proper contrast even from an analysis object on an analysis optical disc. When an image is obtained from an analysis object 111, a control unit (210) switches a switch (208) in such a way that a detection signal of laser light has a constant average value, the laser light having been emitted to the analysis optical disc and reflected thereon or passed therethrough, and the control unit (210) feeds back the output signal of an integrating circuit (209) to an APC circuit (115) for controlling a laser drive circuit (116).

4 Claims, 9 Drawing Sheets

FIG.9

ANALYSIS APPARATUS AND ANALYSIS DISC USED FOR THE SAME

TECHNICAL FIELD

The present invention relates to an analysis apparatus in which an analysis object such as blood is set in an optical disc for analysis and the analysis object is traced and captured as an image.

BACKGROUND ART

As disclosed in National Publication of International Patent Application No. 10-504397 and others, methods are available in which an analysis object to be tested is disposed in a certain portion on a disc, the analysis object is traced, and an image of the analysis object is obtained by using the reproducing function of the optical disc.

Figure 6:
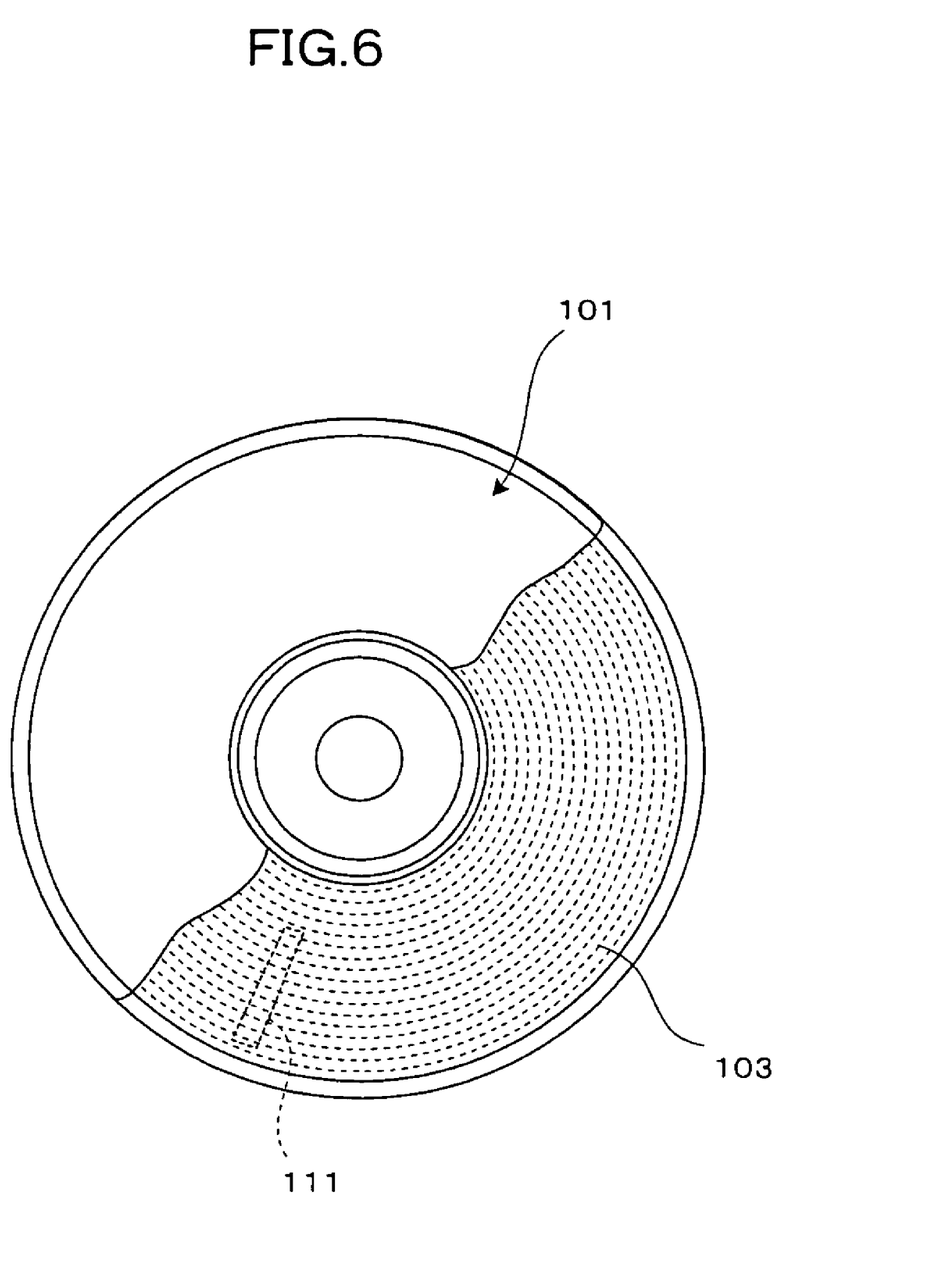
FIG. 6 is a partially cutaway plan view showing a conventional analysis optical disc.
Figure 7:
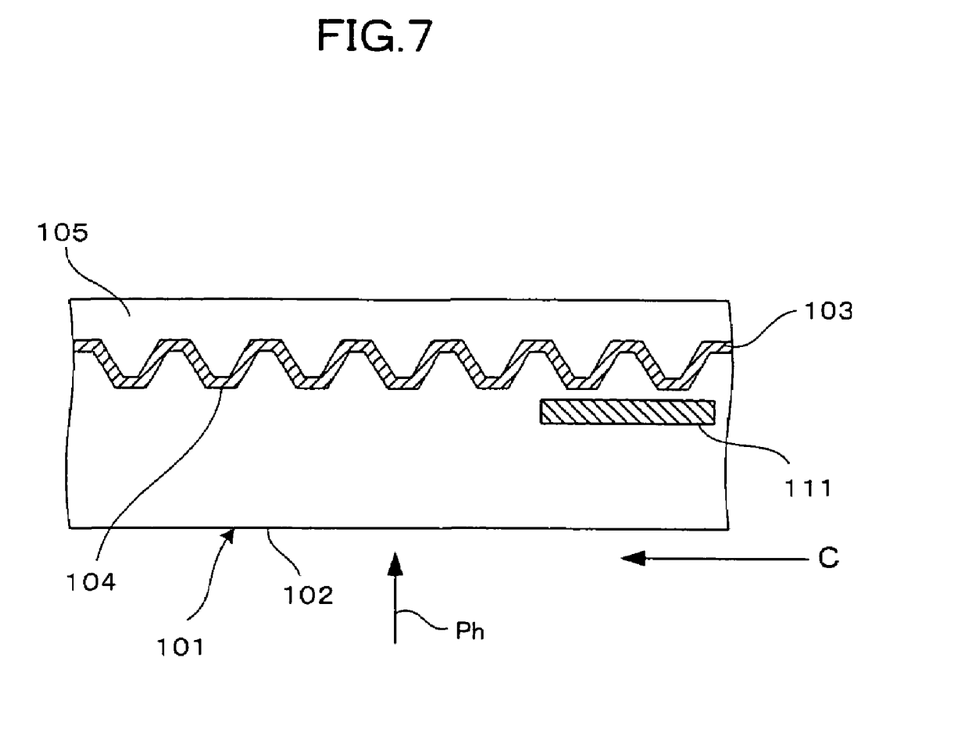
FIG. 7 is a sectional view showing the conventional analysis optical disc.

As shown in FIGS. 6 and 7, an optical disc 101 generally has tracks 103 of an aluminum reflective layer that are formed on a surface of a base 102. Information is recorded on pits and grooves 104 which are asperities finely formed on the tracks. Reference numeral 105 denotes a protective layer.

Figure 5:
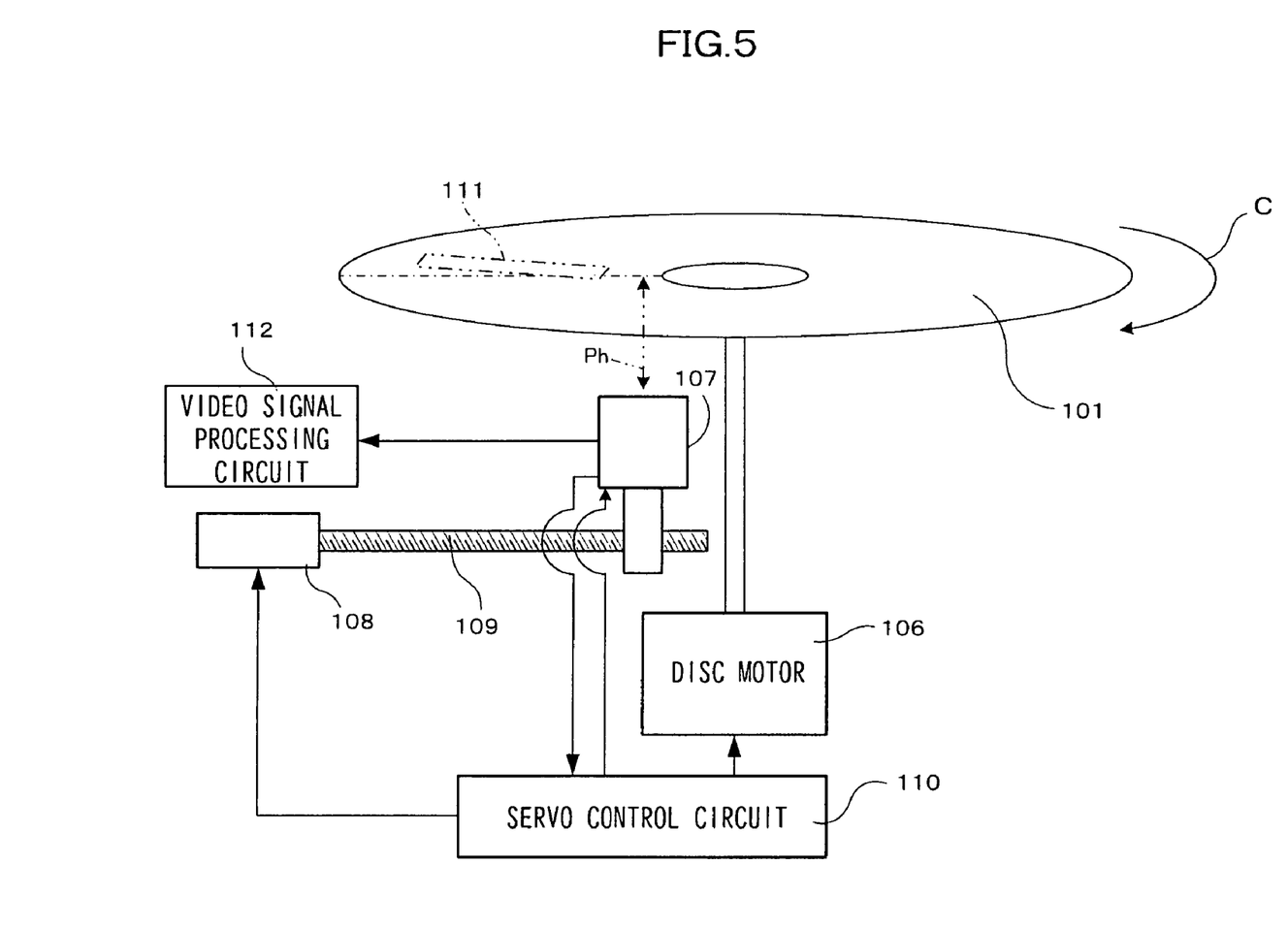
FIG. 5 is a structural diagram showing a typical optical disc drive.

In a typical optical disc drive shown in FIG. 5, reading is performed on the tracks 103 by a laser beam Ph from a pickup 107 while the optical disc 101 is rotated in the direction of arrow C by a disc motor 106. The pickup 107 is screwed onto a feed screw 109 driven by a traverse motor 108. A servo control circuit 110 drives the traverse motor 108 to move the pickup 107 in the radial direction in such a way that the tracks 103 are traced according to the reproduction output of the pickup 107. Further, the servo control circuit 110 detects address information recorded on the tracks 103 and drives (CLV control) the disc motor 106 with a constant linear velocity.

To be specific, the irradiation position of the laser beam Ph on the optical disc 101 is controlled not only by driving the traverse motor 108 but also by driving a tracking actuator (not shown), which is provided in the pickup 107, to control the position of an optical path of the laser beam Ph in the lateral direction (radial direction) with respect to a surface of the optical disc 101 as necessary; meanwhile, the tracks 103 are traced accurately.

Unlike audio CDs and video CDs, in the case of an analysis disc, an analysis object 111 is further disposed in the optical disc 101 as shown in FIGS. 6 and 7. In an analysis apparatus using the technique of a conventional optical disc drive, light reflected from the analysis object 111 is read by a PD (photodetector) 117 of the pickup 107 shown in FIG. 8 and is processed by a video signal processing circuit 112 to obtain an image of the analysis object 111.

Figure 8:
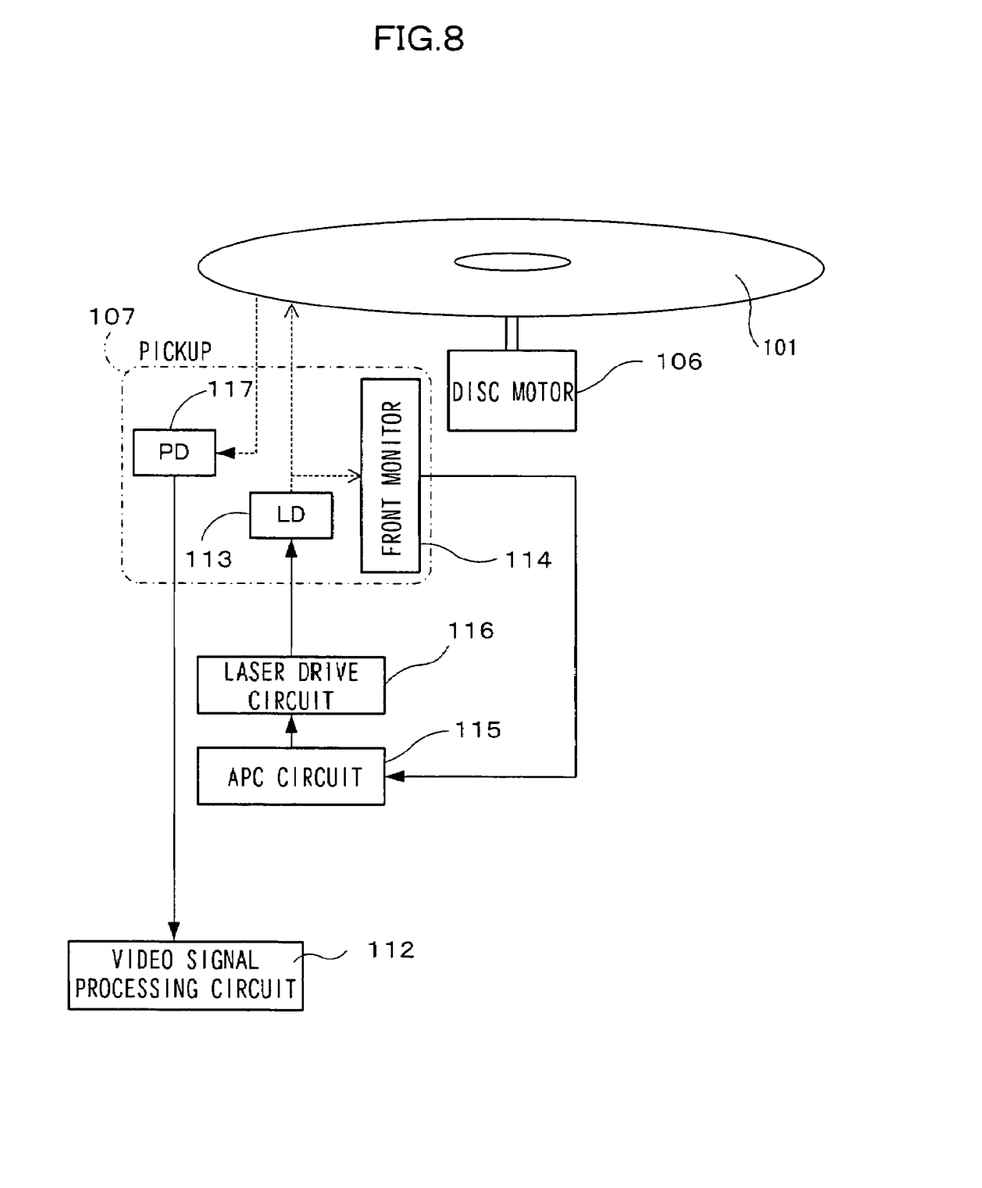
FIG. 8 is a structural diagram showing a power control circuit of a conventional pickup.

FIG. 8 shows a power control circuit of the pickup 107 shown in FIG. 5.

A laser beam output is emitted from an LD (laser LED) 113 of the pickup 107 to the optical disc 101 to read information written on the pits, grooves, and the like of the optical disc 101 and information for each driving servo. The laser beam output is simultaneously emitted to a front monitor 114 serving as a monitor light-receiving element.

The output voltage of the front monitor 114 is inputted to an APC circuit (Auto power control circuit) 115. The APC circuit 115 operates a laser drive circuit 116 in such a way that the front monitor 114 has a constant voltage, and the APC circuit 115 performs feedback control in such a way that the LD 113 has a constant output. The above analysis apparatus is no exception and similar control is performed therein, which effectively acts on stable capturing of signals from the pits, grooves, and the like on the disc.

Figure 9:
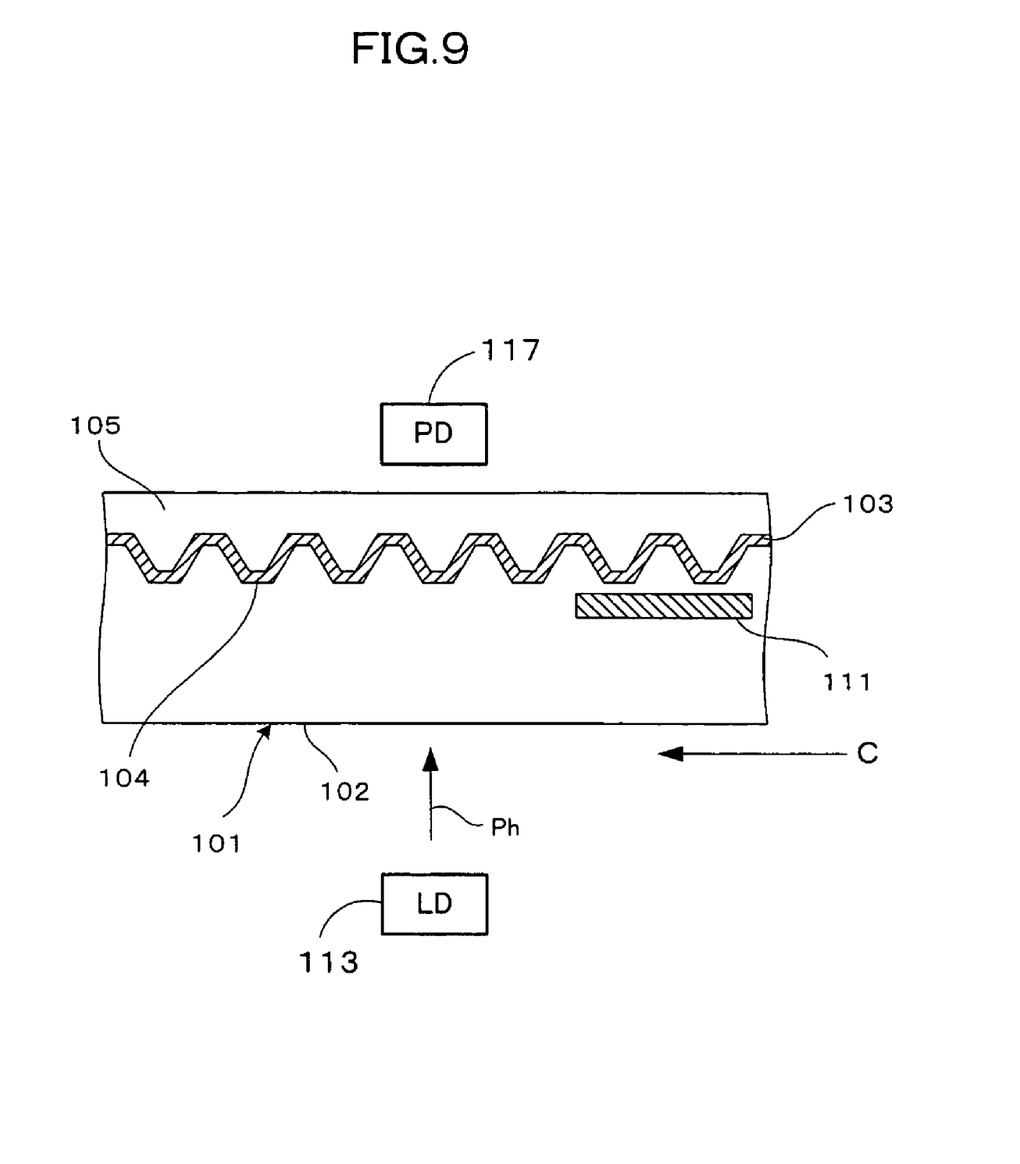
FIG. 9 is a sectional view of the analysis optical disc that shows the arrangement of an LD (laser LED) and a PD (photodetector) of a conventional transmission pickup.

In the optical disc drive shown in FIGS. 5 and 8, the LD 113 and the PD 117 of the pickup 107 are provided on one side of the optical disc 101 to process a detection signal of laser light which has been emitted to and reflected from the optical disc 101. A power control circuit for the pickup 107 of an optical disc drive is configured in the same manner as in FIG. 8. In the optical disc drive, the pickup 107 has the optical disc 101 interposed between the LD 113 and the PD 117 as indicated by a virtual line of FIG. 9 to process a detection signal of laser light which has been emitted to and passed through the optical disc 101.

However, an output for capturing on the pits and grooves is not always optimum as a laser output for obtaining an image of the part of the analysis object 111.

This is because a laser path for obtaining information from the pits and grooves provided in the optical disc 101 is different from a laser path for obtaining an image from the analysis object 111.

DISCLOSURE OF THE INVENTION

It is an object of the present invention to provide an analysis apparatus which can achieve an optimum laser output for obtaining information from pits and grooves and an optimum laser output for obtaining an image from an analysis object 111.

In order to solve the problem, according to the present invention, control is performed according to a contrast of a detected image when an image of the analysis object is obtained. With this configuration, it is possible to obtain an image with an optimum contrast when obtaining the image from the analysis object.

According to the present invention, the analysis apparatus is an analysis apparatus for emitting detection light to an analysis optical disc and reading a state of an analysis object disposed in a part of the analysis optical disc, wherein the apparatus comprises a control unit as a power control system of a laser device for generating laser light emitted to the analysis optical disc, wherein the control unit has a first switching state where the output of the laser light is detected by a monitor light-receiving element and feed back is performed in such a way that the monitor light-receiving element has a constant value, and a second switching state where feedback is performed in such a way that a detection signal of laser light has a constant average value, the laser light having been emitted to the analysis optical disc and reflected thereon or passed therethrough, and the control unit switches the power control system to the first switching state until the detection of a reading position of the analysis object in the analysis optical disc, and switches the power control system to the second switching state at the reading position of the analysis object in the analysis optical disc.

Further, the control unit detects a mark disposed immediately in front of the reading position of the analysis optical disc and switches the power control system of the laser device to the second switching state.

Moreover, the control unit detects a mark disposed immediately in front of the reading position of the analysis optical disc, switches the power control system of the laser device to the second switching state, and returns the power control system to the first switching state after detecting the lapse of specified time.

Besides, the control unit detects a mark disposed immediately in front of the reading position of the analysis optical disc, switches the power control system of the laser device to the second switching state, detects a mark disposed immediately behind the reading position, and switches the power control system to the first switching state.

The analysis disc of the present invention is an analysis disc which can reproduce and trace pits or grooves and has a data area for controlling the rotation of the disc and a reading area having an analysis object disposed therein, wherein a mark is recorded, over the radial direction of the reading area, at a position immediately in front of the reading area in the rotation direction, the analysis object being disposed in the reading area.

Further, the analysis disc of the present invention is an analysis disc which can reproduce and trace pits or grooves and has a data area for controlling the rotation of the disc and a reading area having an analysis object disposed therein, wherein marks are recorded, over the radial direction of the reading area, at positions immediately in front of and behind the reading area in the rotation direction, the analysis object being disposed in the reading area.

BEST MODE FOR CARRYING OUT THE INVENTION

Referring to FIGS. 1 to 4, an embodiment of the present invention will be described below.

The same constituent elements as the conventional art shown in FIGS. 5 to 9 are indicated by the same reference numerals in the following explanation.

Figure 1:
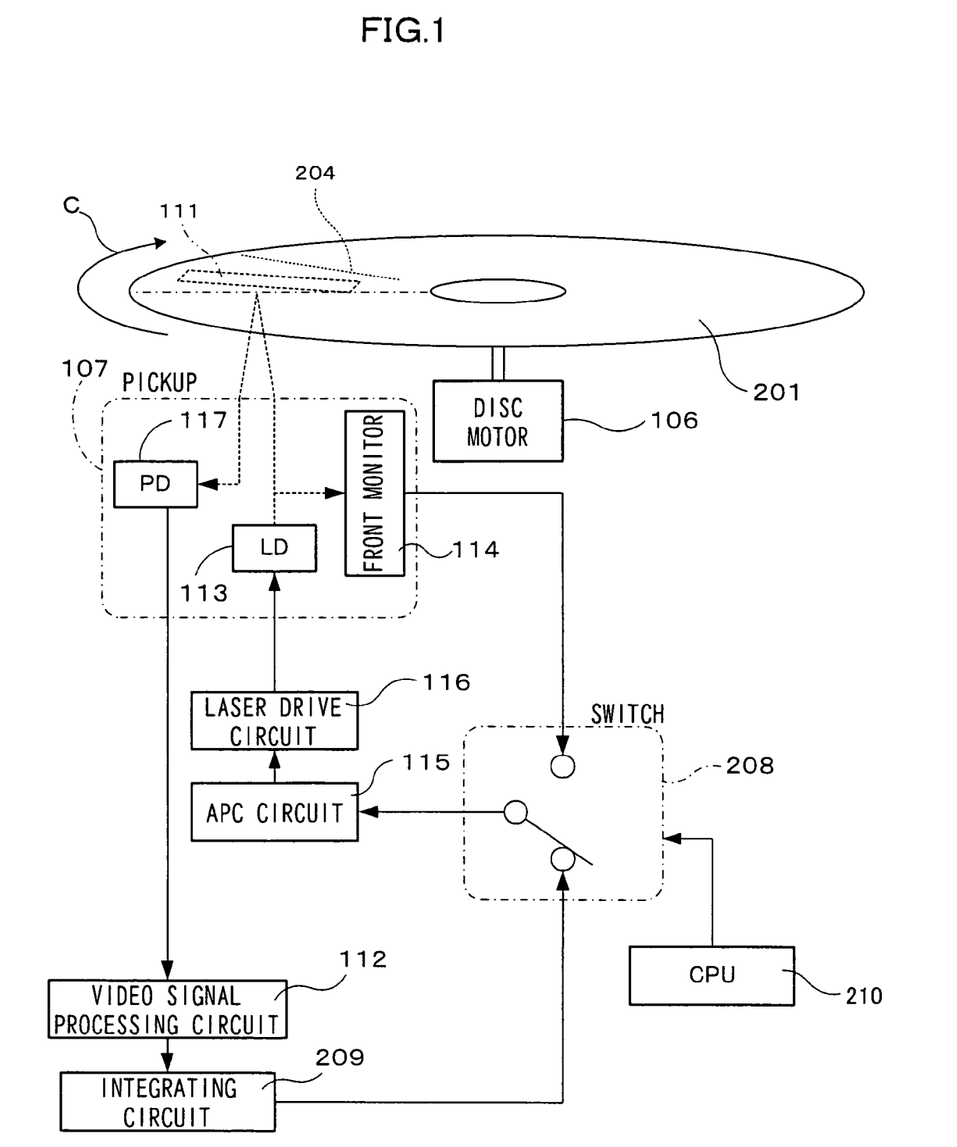
FIG. 1 is a structural diagram showing an analysis apparatus of the present invention.
Figure 2:
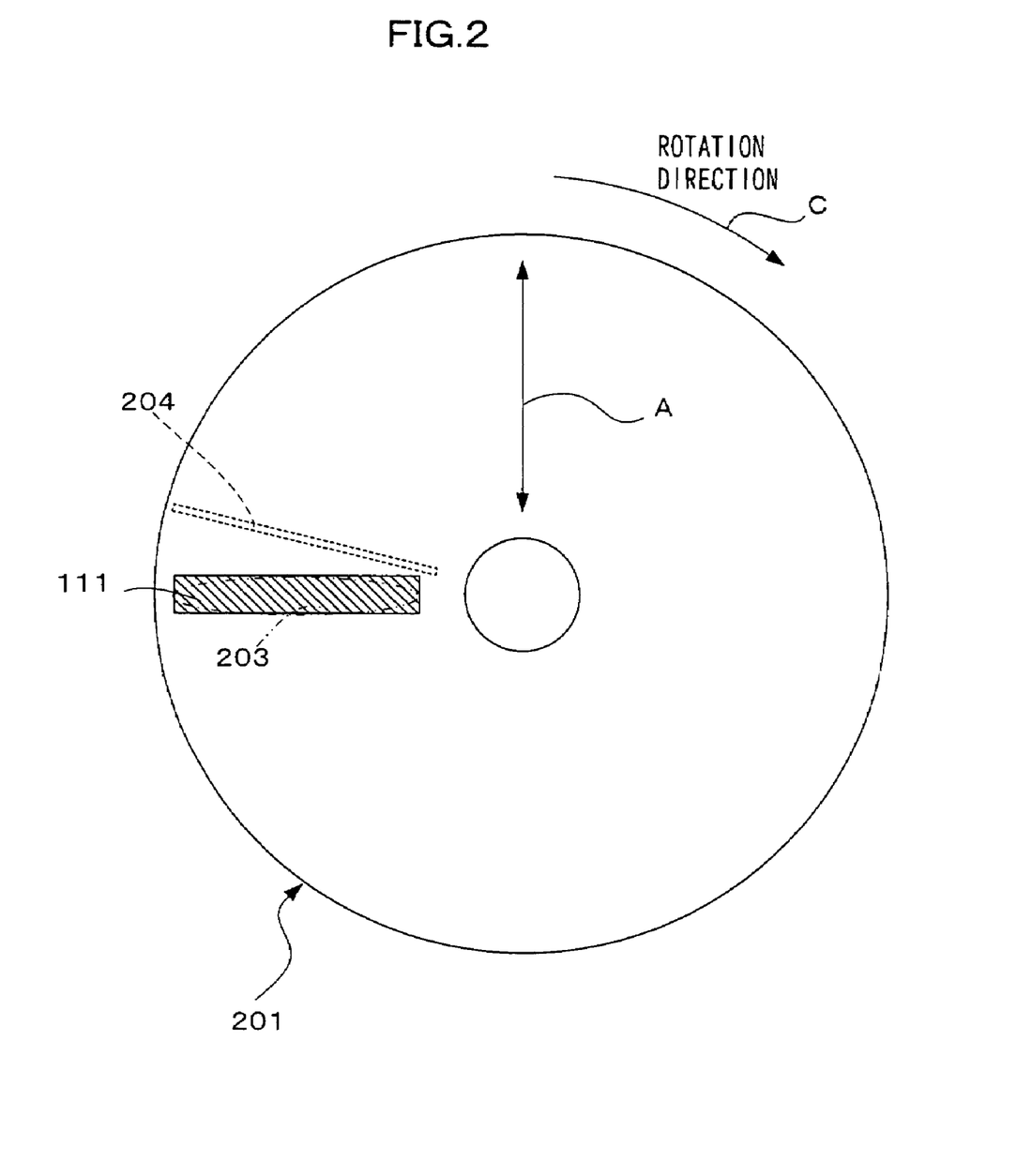
FIG. 2 is a plan view showing an analysis optical disc used in the embodiment.
Figure 3:
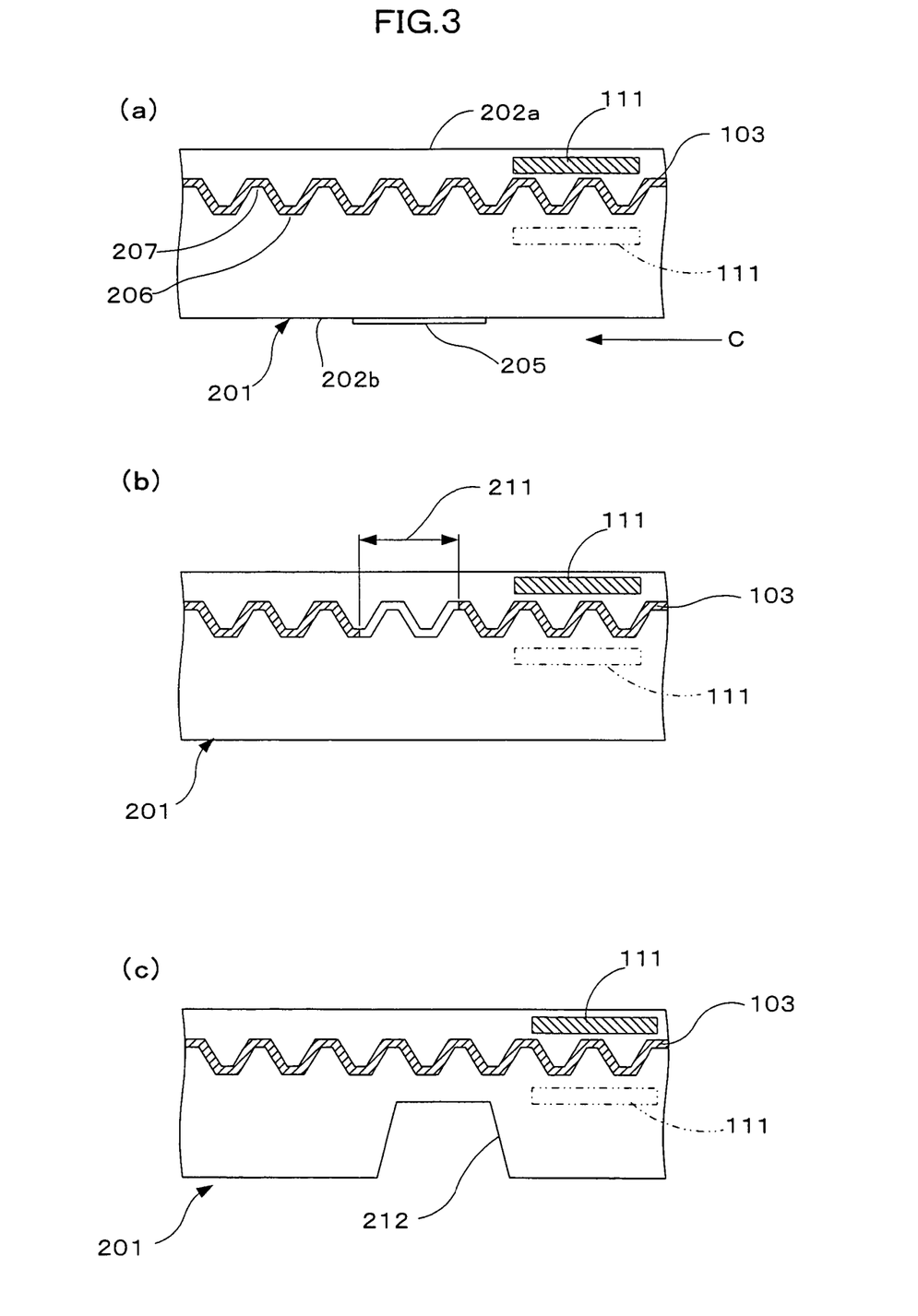
FIG. 3 is a sectional view showing an analysis optical disc of the embodiment.
Figure 4:
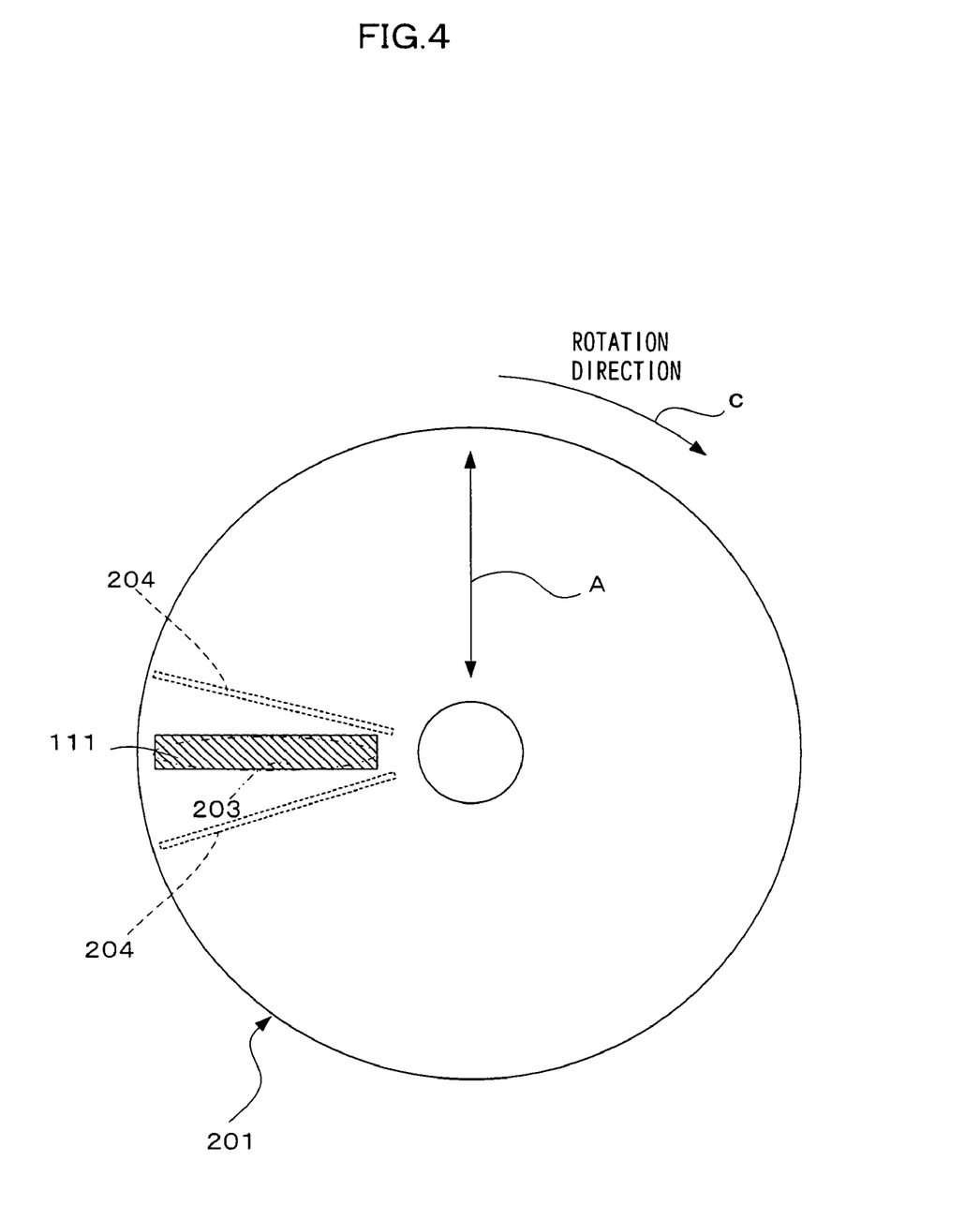
FIG. 4 is a plan view showing the analysis optical disc having marks in front of and behind an analysis object.

FIG. 1 shows a power control circuit for a pickup 107 of an analysis apparatus according to the embodiment of the present invention. FIGS. 2 to 4 show an analysis optical disc 201 used in the analysis apparatus.

First, the analysis optical disc 201 will be discussed below.

As shown in FIG. 2, in the analysis optical disc 201, a mixture of a sample and a reagent corresponding to a test item is set as an analysis object 111. Only at a position immediately in front of a reading area 203 in a rotation direction C, a mark 204 is recorded over the radial direction (the direction of arrow A) of the reading area. The analysis object 111 is disposed in the reading area 203. FIG. 3 shows specific examples of the positions of the analysis object 111 in the analysis optical disc 201 and the mark 204 in the analysis optical disc 201.

As shown in FIG. 3(a), the analysis object 111 is provided between a surface 202a and a track 103 of the analysis optical disc 201. The mark 204 is formed by printing ink 205 and so on like a belt on a back 202b of the analysis optical disc 201. In FIG. 3(a), reference numeral 206 denotes a pit or a groove formed on the track 103 which has been subjected to mirror-like finishing. Reference numeral 207 denotes a land formed on the track 103 which has been subjected to mirror-like finishing.

As indicated by a virtual line of FIG. 3(a), the analysis object 111 may be provided between the track 103 and the back 202b of the analysis optical disc 201.

The power control circuit shown in FIG. 1 switches, by means of a switch 208, an input signal to be fed back to the APC circuit 115. The switch 208 feeds back the output signal of a front monitor 114 or the output signal of an integrating circuit 209 to the APC circuit 115. The switch 208 is controlled by a microcomputer 210 as follows:

When obtaining an EFM signal and a wobble signal on the analysis optical disc 201, the microcomputer 210 switches the switch 208 so as to feed back the output signal of the front monitor 114 to the APC circuit 115, and controls the laser output of the LD 113 in such a way that the front monitor 114 has a constant output voltage.

During an operation in which the laser output of the LD 113 is controlled in such a way that the front monitor 114 has a constant output voltage, when the microcomputer 210 detects the mark 204 from the output signal of the PD 117, the microcomputer 210 automatically switches the switch 208 so as to feed back the output signal of the integrating circuit 209, which integrates the output signal of a video signal processing circuit 112 and outputs the signal, to the APC circuit 115 and the microcomputer 210 enhances contrast on an image of the analysis object 111 of the analysis optical disc 201.

To be specific, light reflected from the analysis object 111 is captured by the PD 117 and inputted to the video signal processing circuit 112. Since the analysis optical disc 201 is traced by a laser light point, reflection of light fluctuates with time due to the analysis object 111. The fluctuation is averaged by the integrating circuit 209 and feedback control is performed on the output of laser light in such a way that an image outputted from the video signal processing circuit 112 has a contrast of an average value.

Further, the microcomputer 210 detects the mark 204 and returns the switch 208, which has been switched so as to feed back the output signal of the integrating circuit 209 to the APC circuit 115, to a state where the output voltage of the front monitor 114 is fed back to the APC circuit 115 after specified time since the detection of the mark 204.

With this configuration, it is possible to achieve an optimum laser output for obtaining information from the pits and grooves, and it is possible to achieve video output with an optimum contrast by means of an optimum laser output for obtaining an image from the analysis object 111.

In this embodiment, the mark 204 is formed by printing the ink 205 like a belt on the back 202b of the analysis optical disc 201. The configuration shown FIG. 35(b) or 35(c) is also applicable.

In FIG. 3(b), the mark 204 can be similarly formed by providing a portion 211 where a mirror surface is partially absent on the track 103, which has been subjected to mirror-like finishing. To be specific, the portion 211 is a BCA (Burst Cutting Area, see DVD specifications, Ver. 1.0 and so on) provided on the mirror surface of a DVD.

In FIG. 3(c), the mark 204 is similarly formed by providing an odd-form portion 212 such as a concave portion partially formed on the outside of the analysis optical disc 201. To be specific, the shape of the disc itself is changed and light reflection is made different from that of a data track surface.

In each embodiment mentioned above, the mark 204 is disposed at a position immediately in front of the reading area 203, which has the analysis object 111 therein, in the rotation direction, and the switch 208 is returned to the original state after specified time since the microcomputer 210 recognizes the mark 204. The following configuration is also applicable: as shown in FIG. 4, a similar mark is disposed at a position immediately behind the analysis object 111 as well as a position immediately in front of the analysis object 111 on the analysis optical disc 201, and the microcomputer 210 detects the mark immediately behind the analysis object 111 and returns the switch 208 to the original state.

In the embodiments, the mark 204 of the analysis optical disc 201 is formed by printing, the removal of a mirror surface, or an odd form. The mark may be provided on the pit or groove 206 or the land 207 of the analysis optical disc 201.

To be specific, the mark is detected by the pickup 107, so that a track data portion and the reading area 203 having the analysis object 111 therein can be discriminated from each other. An example will be discussed below.

The mark is constituted of pits of EFM, MFM, and so on. To be specific, the pits include a prepit and an LPP (land prepit) (a prepit engraved on a track for recording address information on a DVD-R/RW and on a land between the tracks). To be specific, the prepit includes a CAPA (prepit for an address of the DVD-RAM). Some modulation like a wobble is superimposed on the groove or land.

This example is similar to the embodiments in that regarding the mark constituted of pits, grooves, or lands on the analysis optical disc 201, a specific position and a range are a position immediately in front of the reading area 203, which has the analysis object 111 therein, in the rotation direction or a position immediately behind the reading area 203 in the rotation direction.

An analysis apparatus using the analysis disc 201 having the mark formed of pits, grooves, or lands is different from those of the embodiments only in that the pickup 107 reads the mark and generates each trigger signal having detected the position of the mark.

In the embodiments, the LD 113 and the PD 117 are disposed on one side of the optical disc 101 to process a detection signal of laser light having been emitted to and reflected from the optical disc 101. A power control circuit for the pickup 107 of an optical disc drive configured as below acts in the same manner as FIG. 1. In the optical disc drive, the pickup 107 has the optical disc 101 interposed between the LD 113 and the PD 117 to process a detection signal of laser light which has been emitted to and passed through the optical disc 101.

As described above, as a power control system of a laser device for generating laser light emitted to an analysis optical disc, a control unit is provided which has a first switching state where the output of the laser light is detected by a monitor light-receiving element and feedback is performed in such a way that the monitor light-receiving element has a constant value, and a second switching state where feedback is performed in such a way that a detection signal of laser light has a constant average value, the laser light having been emitted to the analysis optical disc and reflected thereon or passed therethrough. The control unit switches the power control system to the first switching state until the detection of a reading position of the analysis object in the analysis optical disc, and switches the power control system to the second switching state at the reading position of the analysis object in the analysis optical disc. Thus, it is possible to achieve an optimum laser output for obtaining information from pits and grooves and an optimum laser output for obtaining an image from the analysis object, thereby achieving an image with a high contrast.

The invention claimed is:

1. An analysis apparatus for emitting detection light to an analysis optical disc and reading a state of an analysis object disposed in a part of the analysis optical disc, wherein
the analysis apparatus comprises a control unit as a power control system of a laser device for generating laser light emitted to the analysis optical disc, wherein
the control unit has a first switching state in which an output of the laser light is detected by a monitor light-receiving element and feedback is performed in such a way that the monitor light-receiving element has a constant value, and a second switching state in which feedback is performed in such a way that a detection signal of laser light has a constant average value, the laser light having been emitted to the analysis optical disc and reflected thereon or passed therethrough, and
the control unit switches the power control system to the first switching state until a reading position of the analysis object in the analysis optical disc is detected, and switches the power control system to the second switching state at the reading position of the analysis object in the analysis optical disc.

2. The analysis apparatus according to claim 1, wherein the control unit detects a mark disposed immediately in front of the reading position of the analysis optical disc and switches the power control system of the laser device to the second switching state.

3. The analysis apparatus according to claim 1, wherein the control unit detects a mark disposed immediately in front of the reading position of the analysis optical disc, switches the power control system of the laser device to the second switching state, and returns the power control system to the first switching state after detecting a lapse of specified time.

4. The analysis apparatus according to claim 1, wherein the control unit detects a mark disposed immediately in front of the reading position of the analysis optical disc, switches the power control system of the laser device to the second switching state, detects a mark disposed immediately behind the reading position, and switches the power control system to the first switching state.

* * * * *